United States Patent [19]

Plummer

[11] Patent Number: 5,600,145
[45] Date of Patent: Feb. 4, 1997

[54] EMISSION/TRANSMISSION DEVICE FOR USE WITH A DUAL HEAD NUCLEAR MEDICINE GAMMA CAMERA WITH THE TRANSMISSION SOURCE LOCATED BEHIND THE EMISSION COLLIMATOR

[75] Inventor: Steven J. Plummer, Hudson, Ohio

[73] Assignee: Picker International, Inc., Highland Heights, Ohio

[21] Appl. No.: 374,977

[22] Filed: Jan. 19, 1995

[51] Int. Cl.⁶ ........................................... G01T 1/166
[52] U.S. Cl. ............................. 250/363.04; 250/363.1; 250/496.1; 250/497.1
[58] Field of Search .......................... 250/497.1, 496.1, 250/363.1, 363.04

[56] References Cited

U.S. PATENT DOCUMENTS 5,210,421  5/1993  Gullberg et al. ................. 250/363.04

FOREIGN PATENT DOCUMENTS 58-92974  6/1983  Japan ................................ 250/363.04
61-235782  10/1986  Japan ................................ 250/363.04

OTHER PUBLICATIONS

Patrick Tan, Dale L. Bailey, Steven R. Meikle, Stefan Eberl, Roger R. Fulton and Brian F. Hutton, "A Scanning Line Source for Simultaneous Emission and Transmission Measurements in SPECT" *The Journal of Nuclear Medicine*, vol. 34, No. 10 (Oct. 1993) pp. 1752–1758.

*Primary Examiner*—Constantine Hannaher
*Attorney, Agent, or Firm*—Fay, Sharpe, Beall, Fagan, Minnich & McKee

[57] ABSTRACT

A SPECT system includes two radiation detector heads (32) and (34) which are mounted opposite each other to a gantry (30) for rotation about a subject. The subject is injected with a source of emission radiation, which emission radiation passes through a collimator (38) mounted on each detector head and is received by a radiation receiving face of the detector heads. A radiation source (40) is disposed between the collimator (38) of one detector head and the face of the one detector head. Transmission radiation from the radiation source (40) passes through the collimator (38), through the subject, and is received by the opposite detector head concurrently with the emission radiation. Alternately, a radiation source (40) is disposed behind the collimator of both detector heads (32, 34) such that both detector heads concurrently receive emission and transmission radiation. The detector heads (32, 34) generate emission and transmission projection data indicative of the received emission and transmission radiation. A sorter (70) sorts the emission and transmission projection data and the data is stored into a projection view memory (72). The emission data is corrected (78) in accordance with the transmission data and into a three-dimensional image representation (80).

17 Claims, 2 Drawing Sheets

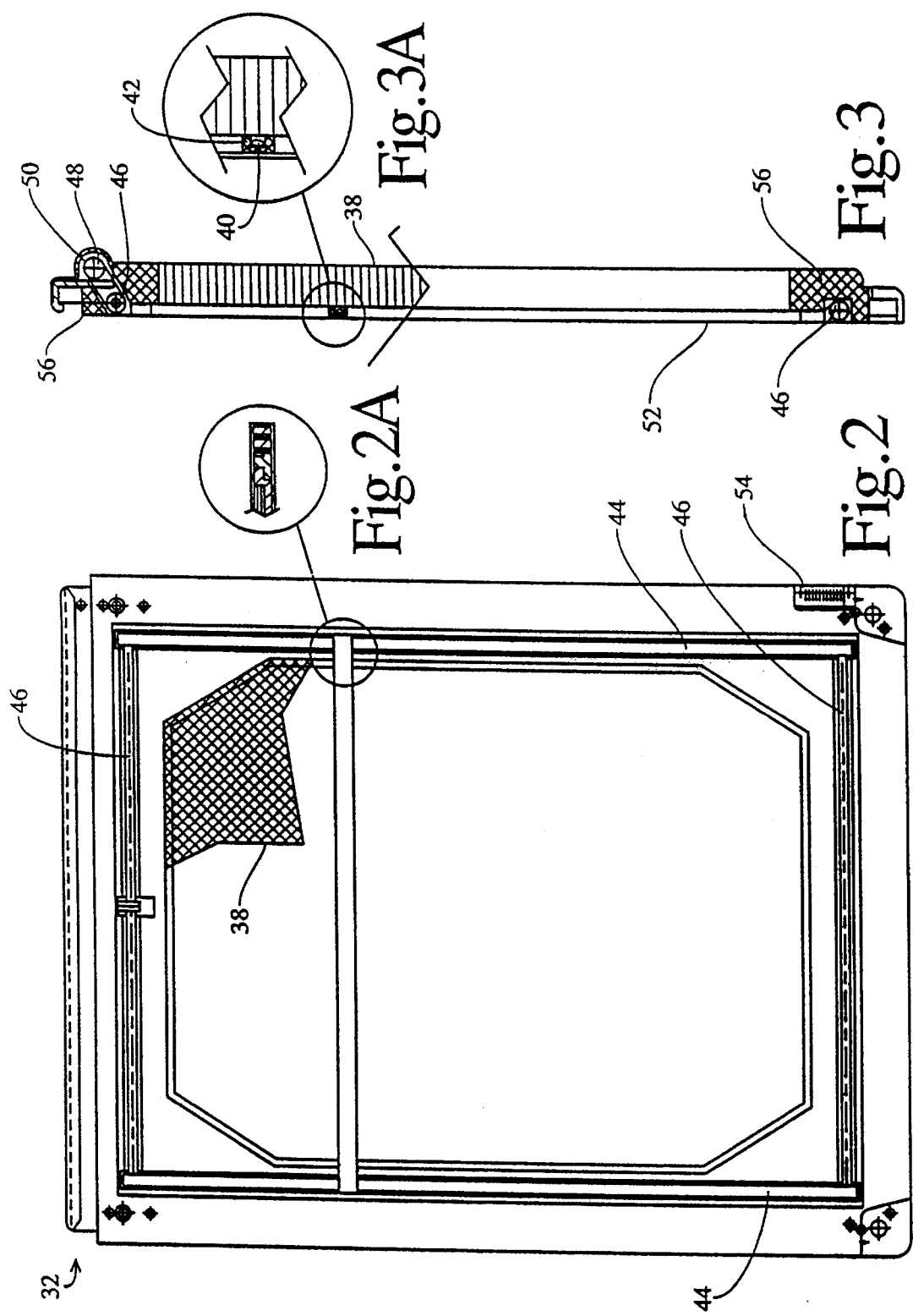

5,600,145

EMISSION/TRANSMISSION DEVICE FOR USE WITH A DUAL HEAD NUCLEAR MEDICINE GAMMA CAMERA WITH THE TRANSMISSION SOURCE LOCATED BEHIND THE EMISSION COLLIMATOR

BACKGROUND OF THE INVENTION

The present invention relates to the art of diagnostic imaging. It finds particular application in conjunction with single-photon emission computed tomography (SPECT) with multi-headed cameras and will be described with particular reference thereto. It is to be appreciated, however, that the invention will also find application in other non-invasive investigation techniques such as positron emission tomography (PET) and other diagnostic modes in which a subject is examined for emitted radiation and with transmitted radiation.

Heretofore, single photon emission computed tomography has been used to study a radionuclide distribution in subjects. Typically, one or more radiopharmaceuticals are injected into a subject. The radiopharmaceuticals are commonly injected into the subject's blood stream for imaging the circulatory system or for imaging specific organs which absorb the injected radiopharmaceuticals. Gamma or scintillation camera heads are placed closely adjacent to a surface of the subject to monitor and record emitted radiation. In single photon-emission computed tomography, the head is rotated or indexed around the subject to monitor the emitted radiation from a plurality of directions. The monitored radiation data from the multiplicity of directions is reconstructed into a three dimensional image representation of the radiopharmaceutical distribution within the subject.

One of the problems with the SPECT imaging technique is that photon absorption and scatter by portions of the subject between the emitting radionuclide and the camera head distort the resultant image. One solution for compensating for photon attenuation is to assume uniform photon attenuation throughout the subject. That is, the subject is assumed to be completely homogeneous in terms of radiation attenuation with no distinction made for bone, soft tissue, lung, etc. This enables attenuation estimates to be made based on the surface contour of the subject. Of course, human subjects do not cause uniform radiation attenuation, especially in the chest.

In order to obtain more accurate radiation attenuation measurements, a direct measurement is made using transmission computed tomography techniques. In this technique, radiation is projected from a radiation source through the subject. Radiation that is not attenuated is received by detectors at the opposite side. The source and detectors are rotated to collect transmission data concurrently with the emission data through a multiplicity of angles. This transmission data is reconstructed into an image representation using conventional tomography algorithms. The radiation attenuation properties of the subject from the transmission computed tomography image are used to correct for radiation attenuation in a the SPECT or other emission data.

In a dual head emission only system, the camera heads are positioned 180° opposite to each other. In a dual head emission/transmission system, the camera heads are positioned at 90° angles from each other so that a radiation source can be positioned directly across from each camera head. The 90° positioning of camera heads avoids positioning one camera head in the same location with one radiation source. In a three camera head system, the heads are positioned at 120° from each other. In this configuration, opposite each camera head is an empty space on the gantry in which a radiation source is positioned.

Placing a radiation source and a camera head in the same location causes several problems. By placing the radiation source, which has a collimator and shielding, in front of the camera head collimator, a significant distance is added between the camera crystal and the subject. A decrease in image resolution occurs in the resulting images. Furthermore, the source holder assembly is difficult to remove when the radiation source is not needed.

The present invention contemplates a new and improved simultaneous transmission and emission tomography method and apparatus for a 180° dual camera head system which overcomes the above-referenced problems and others.

SUMMARY OF THE INVENTION

In accordance with one aspect of the present invention, a simultaneous transmission and emission tomography system is provided. Two radiation detector heads are mounted at 180° from each other around a subject that is injected with an emission radionuclide. Each detector head has a collimator mounted on a radiation receiving face of each detector head for limiting radiation received by the detector heads. A transmission radiation source is disposed between the collimator of one detector head and the radiation receiving face of the same detector head. The opposite detector head receives both the emission radiation from the subject and the transmission radiation from the transmission radiation source. Emission and transmission projection data is produced indicative of the received emission and transmission radiation. A reconstruction processor reconstructs a volumetric image representation from the emission and transmission projection data.

In accordance with another aspect of the present invention, a radiation source shield surrounds a portion of the transmission radiation source to limit the direction of the transmission radiation.

In accordance with a more limited aspect of the present invention, a radiation source driver moves the transmission radiation source from one side of the collimator to the other side. A shielded area is disposed at one or both sides of the collimator. The radiation source is positioned within the shielded area when the radiation source is not in use. The shielded area shields all transmission radiation transmitted from the transmission radiation source.

In accordance with another aspect of the present invention, both detector heads have a transmission radiation source disposed between their collimators and the radiation receiving face of the detector head. Both detector heads simultaneously collect emission and transmission radiation.

In accordance with another aspect of the present invention, emission and transmission projection data is generated from the received emission and transmission radiation. The emission and transmission projection data is separated and stored in a projection data memory. The emission projection data is corrected in accordance with the transmission projection data.

One advantage of the present invention is that simultaneous emission and transmission radiation can be collected by 180° opposite detector heads.

Another advantage of the present invention is that positioning the radiation source between the collimator and the detector face allows the same collimator to be used for collimating both the emission and transmission radiation.

Another advantage of the present invention is that the radiation source does not interfere with positioning the camera head close to the subject.

Another advantage of the present invention is that by mounting the radiation source to the collimator assembly allows the drive assembly of the radiation source to be easily mounted and dismounted from the detector.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2 is an illustration of a collimator and radiation source mounted on a radiation receiving face of a detector, in partial section;

FIG. 2A is an enlarged sectional view of a portion of FIG. 2;

FIG. 3 is a cross-sectional side view of a collimator and radiation source in accordance with the present invention; and FIG. 3A is an enlarged view of a portion of FIG. 3.

DETAILED DESCRIPTION OF THE PREFERRED EMBODIMENTS

Figure 1:
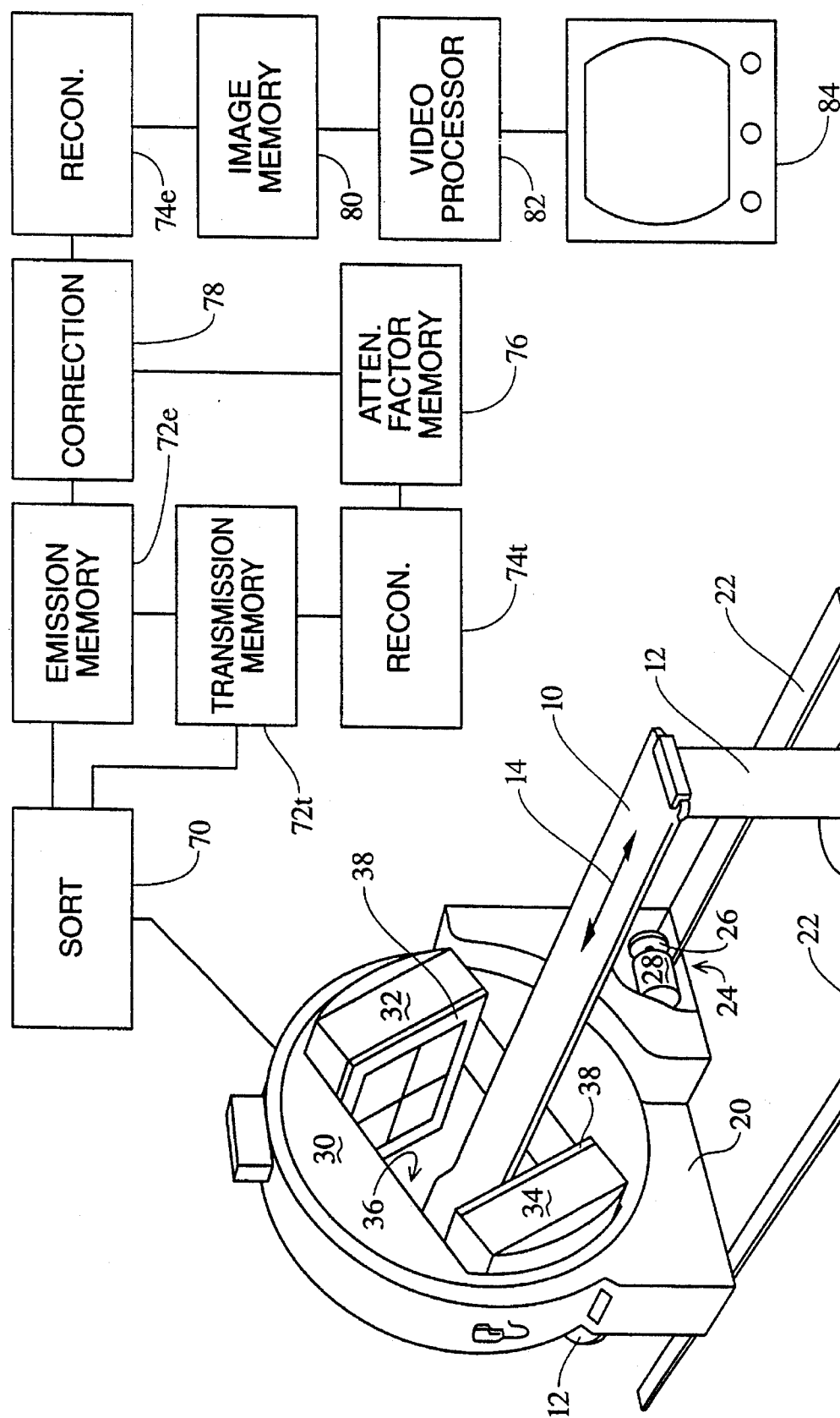
FIG. 1 is a perspective view of a gamma camera system in accordance with the present invention.

With reference to FIG. 1, a subject support or table 10 is mounted to stationary, vertical supports 12 at opposite ends. The subject table is selectively positionable up and down to center the subject in the center of a circle along a longitudinal axis 14.

An outer gantry structure 20 is movably mounted on tracks 22 which extend parallel to the longitudinal axis. This enables the outer gantry structure to be moved parallel to the longitudinal axis 14. An outer gantry structure moving means 24 is provided for selectively moving the outer gantry structure 20 along the rails 22 in a path parallel to the longitudinal axis. In the illustrated embodiment, the longitudinal moving means includes drive wheels 26 for supporting the outer gantry structure on the tracks. A motive power means, such as a motor 28, selectively drives one of the wheels which frictionally engages the track and drives the outer gantry structure and supported inner gantry structure and detector heads therealong. Alternately, the outer gantry can be stationary and the subject support configured to move the subject along the longitudinal axis.

An inner gantry structure 30 is rotatably mounted on the outer gantry structure 20. A first camera or detector head 32 is movably mounted to the inner gantry structure. A second detector head 34 is movably mounted to the inner gantry structure opposite to the first camera head. The detector heads are independently movable toward and away from each other. The inner gantry structure defines a central, subject receiving aperture 36 for receiving the subject table and, particularly along the longitudinal axis. The aperture 36 is enlarged to receive the detector heads in any of a variety of displacements from a central axis and angular orientations.

The detector heads have collimators 38 removably mounted on a front face to restrict received radiation to radiation traveling generally perpendicular to the face. The face includes a scintillation crystal that emits a flash of light in response to incident radiation. An array of photomultiplier tubes convert the light into electrical signals. A resolver circuit resolves the x,y-coordinates of each light flash and the energy of the incident radiation.

With reference to FIGS. 2 and 3, a radiation source 40 is mounted directly behind the collimator, between the collimator 38 and the detector face 42. In the preferred embodiment, the radiation source 40 is a line source extending across the collimator 38. In the preferred embodiment, the line source is a thin steel tube that is filled with a radionuclide and sealed at its ends.

Optionally, the radiation source may be a bar source, a point source, a flat rectangular source, a disk source, a flood source, a tube or vessel filled with a radionuclide, or an active radiation generator such as an x-ray tube. The radiation source 40 and the collimator 38 are mounted abutting the face of the detector head. The collimator is positioned a short distance away from the detector face in order to create space for the radiation source. The radiation source 40 is disposed into a source holder 44 made from a radiation blocking material, such as lead. The source holder 44 partially encases the radiation source and serves as a radiation shield to limit the projection of radiation only towards the collimator and into the examination region. The source holder blocks radiation from the source from striking the detector face and causing stray radiation events.

With further reference to FIGS. 2 and 3, a drive mechanism having belts 46 selectively moves the source holder 44 and the radiation source 40 across the collimator. The belts are driven by an arrangement of shafts 48, pulleys 50, and a gear motor 52 in the preferred embodiment. Other drives for moving the source, such as screwdrivers, pneumatic drives, and the like, are also contemplated. The radiation source 40, the source holder 44, and drive mechanism are covered within a thin sheet or cover 54. The source holder 44 is readily removable from the drive mechanism in order to replace the radiation source 40. Electrical power to the drive mechanism and feedback signals indicative of the actual position of the source are transmitted to control circuitry through a power connector 56.

At each end of the radiation source motion range, is a shielded park position 58, in which the open side of the source holder is covered by a lead or other radiation blocking shield 60. While the source holder 44 is in the park position, the radiation from the radiation source 40 is blocked in all directions. Thus, the subject is prevented from receiving a higher radiation dose than is necessary to create the transmission image. After each scan of the radiation source, the source holder 44 remains in the park position until the gantry increments or rotates to a next angular scan position. The shielded park position 58 also prevents an operator from being exposed to radiation during collimator exchange, transport, and storage.

Conventional gamma detector heads image radiation in two or more energy windows or ranges simultaneously. In a conventional dual energy gamma detector head, the sum signals are sorted based on amplitude. More specifically, energy windows or ranges are defined. Each window corresponds to a photopeak or energy spectrum of a radionuclide to be used in the examination. In the preferred embodiment, the injected or emission radionuclide has one preselected energy and the radiation source 40 or transmissive radiation has a second, different energy. In this manner, the detector heads 32 and 34 separate the transmission and emission radiation data by using the conventional energy separation circuitry used during dual injected radiopharmaceutical examinations. A position resolver (not shown) resolves the position on the crystal, hence the ray angle, corresponding to scintillations or radiation events within each of the energy windows.

During a scanning operation, the collimator 38 of the preferred embodiment limits the emission and transmission radiation received by the detector face to radiation travelling generally perpendicular to the face. The non-perpendicular radiation is primarily absorbed by the collimator walls. Concurrently, the radiation source 40 and source holder 44 are moved across the length of the collimator by the drive mechanism. The transmission radiation from the radiation source 40 is also restricted by its associated collimator such that only radiation that is substantially parallel to the collimator is allowed to pass through the collimator towards the subject. Thus, radiation which is not useful in creating a transmission image is prevented from being transmitted and absorbed by the subject. The transmission radiation from the radiation source which passes through the collimator enters the subject and is attenuated by the subject and received by the opposite detector. The transmission radiation received by the opposite detector is used to create transmission projection data.

With reference again to FIG. 1, emission radiation from the subject is received by both detector heads 32 and 34 and emission projection data is generated. The emission data normally contains inaccuracies caused by varying absorption characteristics of the subject's anatomy. A sorter 70 sorts the emission projection data and transmission projection data on the basis of the relative energies. The data are stored in a projection view memory 72, more specifically in corresponding emission data memory 72e and transmission data memory 72t. A reconstruction processor 74t reconstructs the transmission data into a transmission image representation or volume of attenuation factors stored in a memory 76. Each voxel value stored in the memory 76 is indicative of attenuation of tissue in a corresponding location within the patient. An emission data correction means 78 corrects the emission data in accordance with the attenuation factors determined from the transmission data. More specifically, for each ray along which emission data is received, the emission correction means calculates a corresponding ray through the transmission attenuation factors stored in the memory 76. Each ray of the emission data is then weighted or corrected 78 in accordance with the attenuation factors and reconstructed by an emission radiation reconstruction processor 74e to generate a three-dimensional emission image representation that is stored in a volumetric image memory 80. A video processor 82 withdraws selected portions of the data from the image memory 80 to generate corresponding human-readable displays on a video monitor 84. Typical displays include reprojections, selected slices or planes, surface renderings, and the like.

In an alternative embodiment, a radiation source 40 is disposed behind each collimator 38 of each detector head. Each detector head receives both emission and transmission radiation and generates corresponding emission and transmission projection data.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A diagnostic imaging system comprising:

a gantry for movably supporting first and second detector heads oppositely disposed on the gantry, each detector head receiving emission radiation from an examination region and generating emission data indicative thereof;

first and second collimators mounted on radiation receiving faces of the first and second detector head, respectively, for collimating the radiation received by the first and second detector heads;

a transmission radiation source mounted to traverse along the first collimator between the radiation receiving face of the first detector head and the examination region such that the second detector head receives both emission radiation from the examination region and transmission radiation from the transmission radiation source, the second detector head further generating transmission data indicative of the transmission radiation received;

a radiation blocking shield mounted to traverse along the first collimator with the transmission radiation source, the radiation blocking shield being disposed between the transmission radiation source and the first detector head radiation receiving face such that the transmission radiation is blocked from being received by the first detector head; and a reconstruction processor for reconstructing a volumetric image representation from the emission and transmission data.

2. The diagnostic imaging system as set forth in claim 1 further including:

a radiation source driver which moves the transmission radiation source longitudinally across the first collimator.

3. The diagnostic imaging system as set forth in claim 2 further including:

a shielded area disposed at least at one side of the first collimator such that when the radiation source is positioned within the shielded area, transmission radiation is contained within the shielded area.

4. The diagnostic imaging system as set forth in claim 1 further including:

a second transmission radiation source disposed between the second detector head and the collimator of the second detector head such that the first detector head receives both emission radiation from the examination region and transmission radiation from the second transmission radiation source, the first detector head generating transmission data indicative of the transmission radiation received from the second transmission radiation source.

5. The diagnostic imaging system as set forth in claim 1 further including:

a sorter for sorting the emission and transmission data generated;

a memory for storing the emission and transmission data;

an emission data correction means for correcting the emission data in accordance with the transmission data and supplying the corrected emission data to the reconstruction processor.

6. The diagnostic imaging system as set forth in claim 1 wherein the first collimator defines a pair of guide members longitudinally along oppositely disposed side regions thereof, the radiation blocking shield and the transmission radiation source being mounted for translating movement along the guide members.

7. The diagnostic imaging system as set forth in claim 6 wherein the radiation blocking shield includes a generally U-shaped radiation blocking element which carries the transmission radiation source therein, the generally U-shaped element having an opening disposed toward the first collimator and being closed toward the first detector head, such that transmission radiation is emitted through the first collimator as the U-shaped element moves along the guide members.

8. The diagnostic imaging system as set forth in claim 7 further including at ends of the guide members, a radiation blocking shield which interacts with the opening of the U-shaped member to block the passage of transmission radiation.

9. The diagnostic imaging system as set forth in claim 1 wherein the radiation blocking shield, is disposed around the radiation source such that the transmission radiation is transmitted only in a direction towards the examination region.

10. The diagnostic imaging system as set forth in claim 1 wherein the transmission radiation source includes one of:
   a line source;
   a bar source;
   a point source;
   a flat rectangular source;
   a disk source; and,
   a flood source.

11. A diagnostic imaging system comprising:
   a gantry for movably supporting first and second detector heads oppositely disposed on the gantry, each detector head receiving emission radiation from an examination region and generating emission data indicative thereof;
   a first collimator grid mounted between the radiation receiving face of the first detector head and the examination region, for collimating the radiation received by the first detector head;
   a second collimator grid mounted between the radiation receiving face of the second detector head and the examination region, for collimating the radiation received by the second detector head;
   a movable transmission radiation source movably disposed between the first detector head and a front face of the first collimator grid, the second detector head receiving both emission radiation from the examination region and transmission radiation from the transmission radiation source, the second detector head further generating transmission data indicative of the transmission radiation received;
   a radiation source shield surrounding a portion of the transmission radiation source such that transmission radiation from the transmission radiation source is directed toward the second detector head and blocked from being received by the first detector head; and
   a reconstruction processor for reconstructing a volumetric image representation from the emission and transmission data.

12. In a diagnostic imaging system for examining a subject in an examination region who has been injected with a radiopharmaceutical having a first characteristic energy level, the imaging system including a pair of detector heads oppositely mounted across the examination region for receiving emission radiation emitted by the radiopharmaceutical and a reconstruction processor for reconstructing an image representation based on the radiation received by the detector heads, each detector head having a collimator mounted on a radiation receiving face of the detector heads, the improvement comprising:
   a transmission radiation source movably disposed between the collimator of one of the detector heads and its radiation receiving face, the transmission radiation source selectively transmitting transmission radiation having a second characteristic energy level through the collimators such that the other detector head concurrently receives both the emission radiation and the transmission radiation while the one detector head is shielded from receiving transmission radiation from the transmission radiation source.

13. A collimator for diagnostic imaging systems which include a detector head which has a radiation receiving face for receiving emission radiation from a subject which has been injected with a radiopharmaceutical, which radiation has passed through the collimator, the collimator comprising:
   a series of vanes, the vanes extending between a subject facing surface and a detector head facing surface;
   a guide assembly disposed along the detector head facing surface of the vanes;
   a carrier for carrying a transmission radiation source mounted to the guide assembly, the carrier being selectively translatable along the guide assembly behind the vanes such that the carrier temporarily blocks the emission radiation from reaching a portion of the radiation receiving face of the associated detector head during translation, the carrier blocking radiation from the carried transmission radiation source from impinging on the radiation receiving face of the associated detector head and directing the radiation from the carried radiation source through the vanes of the collimator toward the subject, whereby the radiation source carrier is selectively translatable along the guide assembly to transmit radiation toward the subject while the detector head radiation receiving face is receiving radiation emitted by the radiopharmaceutical injected into the subject.

14. A method of diagnostic imaging with a camera system including a first detector head having a first collimator mounted adjacent a radiation receiving face thereof and a second detector head having a second collimator mounted adjacent a radiation receiving face thereof, the first and second detector heads being disposed on opposite sides of an examination region and rotatable therearound, the method comprising:
   injecting a radiopharmaceutical into a subject in the examination region, the radiopharmaceutical emitting radiation of a first characteristic energy;
   moving a radiation source along the first collimator between the first detector head radiation
   receiving face and the examination region shielding a portion of the first detector head radiation face from receiving radiation emitted by the radiopharmaceutical, the radiation source being configured to transmit radiation toward the examination region;
   shielding the radiation source to block radiation transmitted by the radiation source from being received by the first detector head;
   moving the detector heads around the examination region;
   with the first detector head, receiving radiation emitted by the radiopharmaceutical;

with the second detector head, receiving radiation transmitted from the radiation source and radiation emitted by the radiopharmaceutical through the second collimator.

15. The method of diagnostic imaging as set forth in claim 14 further including:

separating output signals from the first and second detector heads which are attributable to emission radiation from output signals which are attributable to transmission radiation;

correcting the emission radiation output signals in accordance with the transmission radiation output signals;

reconstructing the corrected emission radiation output signals into an image representation.

16. The method of diagnostic imaging as set forth in claim 14 further including moving a second radiation source between the second detector head radiation receiving face and the second collimator such that the second radiation source transmits radiation through the second collimator toward the examination region and the first detector head.

17. The diagnostic imaging method as set forth in claim 14 further including:

when the radiation source has been moved fully to one side of the radiation receiving face, shielding the radiation source to block radiation from being transmitted.

* * * * *